United States Patent
Hoock et al.

(10) Patent No.: US 9,149,468 B2
(45) Date of Patent: Oct. 6, 2015

(54) MULTICOMPONENT CRYSTALS MADE ([2-AMINO-6-(4-FLUORO-BENZYLAMINO)-PYRIDIN-3-YL]-CARBAMIC ACID ETHYL ESTER AND 2-[2-[(2,6-DICHLORPHENYL)-AMINO]-PHENYL]-ACETIC ACID

(75) Inventors: Christoph Martin Hoock, Dresden (DE); Asal Qadan, Dresden (DE); Bernd Terhaag, Dresden (DE)

(73) Assignee: TEVA GmbH, Ulm (DE)

( * ) Notice: Subject to any disclaimer, the term of this patent is extended or adjusted under 35 U.S.C. 154(b) by 0 days.

(21) Appl. No.: 13/992,247

(22) PCT Filed: Dec. 20, 2011

(86) PCT No.: PCT/EP2011/073441
§ 371 (c)(1),
(2), (4) Date: Jun. 7, 2013

(87) PCT Pub. No.: WO2012/084975
PCT Pub. Date: Jun. 28, 2012

(65) Prior Publication Data
US 2013/0261157 A1    Oct. 3, 2013

(30) Foreign Application Priority Data
Dec. 20, 2010   (DE) .......................... 10 2010 063 612

(51) Int. Cl.
| A61K 31/44 | (2006.01) |
| A61K 31/196 | (2006.01) |
| C07C 229/42 | (2006.01) |
| C07D 213/75 | (2006.01) |

(52) U.S. Cl.
CPC .............. *A61K 31/44* (2013.01); *A61K 31/196* (2013.01); *C07C 229/42* (2013.01); *C07D 213/75* (2013.01)

(58) Field of Classification Search
None
See application file for complete search history.

(56) References Cited

U.S. PATENT DOCUMENTS

| 4,778,799 A * | 10/1988 | Tibes et al. ................... 514/277 |
| 5,959,115 A | 9/1999 | Olbrich et al. |
| 7,553,858 B2 | 6/2009 | Szelenyi et al. |
| 2008/0039463 A1 | 2/2008 | Nadeson et al. |
| 2009/0306150 A1 * | 12/2009 | Hoock et al. ................... 514/352 |
| 2011/0092482 A1 | 4/2011 | Nadeson et al. |
| 2012/0277271 A1 | 11/2012 | Nadeson et al. |

FOREIGN PATENT DOCUMENTS

| CN | 1917876 A | 2/2007 |
| DE | 3601195 | 7/1986 |
| DE | 197 05 555 | 8/1998 |
| EP | 0 207 193 | 1/1987 |
| EP | 2 123 626 | * 11/2009 .............. C07C 59/64 |
| EP | 2 123 626 A1 | * 11/2009 |
| WO | 2007/128056 | 11/2007 |
| WO | 2009/152142 | 12/2009 |

OTHER PUBLICATIONS

O'Connor et al. in International Journal of Pharmaceutics 226 (2001) 163-179.*
Morissette et al. in Advanced Drug Delivery Reviews 56 (2004) 275-300.*
Brogden et al. in Drugs 20(1), 22-48 (1980).*
Devulder, J. in CNS Drugs 24(10), 867-881 (2010).*
Morissette et al. in Drug Delivery Reviews, 56 (2004) 275-300.*
Diamantis W. et al: Analgesic activity following combined oral administration of flupirtine maleate and peripherally acting analgesics in mice and rats; Postgraduate Medical Journal (1987) 63, 29-34.
Kornhuber L. et al.: Flupirtine shows functional NMDA receptor antagonism by enhancing Mg2+ block via activation of voltage independent potassium channels; Journal of Neural Transmission (1999) 106; 857-867; cited in instant specification (p. 1; 3rd paragraph).
Kornhuber L. et al.: Neuronal Kaliumkanalöffnung durch Flupirtin; Fortschr. Neurol. Psychiat. 67 (1999) 466-475; Georg Thieme Verlag Stuttgart—New York; see English Abstract ; cited in instant specification (p. 1; 3rd paragraph).

* cited by examiner

*Primary Examiner* — Dennis Heyer
(74) *Attorney, Agent, or Firm* — Gudrun E. Huckett

(57) ABSTRACT

The invention relates to novel multicomponent crystals, to the production thereof, and to the use thereof for treating pain conditions, in particular of unclear genesis, by means of a simultaneous effect on pains which are caused by muscle tension or degenerative joint diseases as well as on pains that are based on inflammatory processes. The novel multicomponent crystals contain ([2-amino-6-(4-fluoro-benzylamino)-pyridin-3-yl]-carbamic acid ethyl ester (flupirtine) and 2-[2-[(2,6-dichlorphenyl)-amino]-phenyl]-acetic acid (diclofenac) as the sole active ingredient combination and can be produced by dissolving the two components in a molar ratio of 1.0:0.9 to 1.0:1.1 in an inert organic solvent and subsequently crystallizing the complex compound.

20 Claims, 6 Drawing Sheets

MULTICOMPONENT CRYSTALS MADE ([2-AMINO-6-(4-FLUORO-BENZYLAMINO)-PYRIDIN-3-YL]-CARBAMIC ACID ETHYL ESTER AND 2-[2-[(2,6-DICHLORPHENYL)-AMINO]-PHENYL]-ACETIC ACID

BACKGROUND OF THE INVENTION

The present invention concerns novel multicomponent crystals of ([2-amino-6-(4-fluoro-benzylamino)-pyridin-3-yl] carbamic add ethyl ester and 2-[2-[(2,6-dichlorophenyl)-amino]-phenyl] acetic add, their manufacture as well as their use in pharmaceutical preparations. The multicomponent crystals according to the invention are suitable for treatment of pain conditions, in particular of unclear genesis, by a simultaneous action on pains that are caused by muscle tension or degenerative joint diseases as well as on those that are caused by inflammatory processes.

([2-amino-6-(4-fluoro-benzylamino)-pyridin-3-yl] carbamic acid ethyl ester, also known as flupirtine, is a centrally acting non-opioid analgesic agent that is free of the typical side effects of natural or synthetic opioids such as, for example, respiratory depression, constipation, development of drug tolerance, physical or psychological dependence or risk of addiction, Flupirtine is an active ingredient that can normalize an increased muscular tone.

Flupirtine is the prototype of a new class of analgesics with new specific and therapeutically relevant properties. In this context, the mode of action of flupirtine is not based on a direct but on an indirect functional NMDA antagonistic effect. This mechanism results in three different action principles: analgesic, muscular tone-reducing, and neuroprotective. The various actions of flupirtine are the result of a single molecular action mechanism, i.e., the action of flupirtine as a selective neuronal potassium channel opener (selective neuronal potassium channel opener=SNEPCO) (see, for example, Kornhuber J et al. (1999); Kornhuber J et al. (1999a)) that represents a new principle in pain therapy.

As a result of these multiple actions, flupirtine exhibits a unique and broad pharmacological action spectrum. Flupirtine is suitable for treatment and prophylaxis of acute and chronic pain, including neuropathic pain, nerve pain, pain caused by cancer diseases, vasomotoric and migraine headaches, pain conditions after operations, after injuries, burns, in case of dysmenorrhea, toothache and arthritic pain.

Anti-inflammatory effects of flupirtine are to be expected for conventional analgesic dosages only to a minimal degree because a significant anti-inflammatory action has been observed in animal experiments only upon very high dosages (>30 mg per kg body weight). Flupirtine is primarily effective in the treatment and prophylaxis of pains that in particular are caused by muscle tension, muscle spasms and muscle stiffness. It is particularly effective for the treatment of back pain wherein a clear differentia diagnosis regarding the genesis of this tension-caused back pain in the meaning of inflammatory and/or non-inflammatory causes cannot always be determined unequivocally in an individual case.

Flupirtine maleate can be combined with various pain relievers, for example, with morphine (EP 0977736), with neurokinin antagonists (WO 2007/128056) with tramadol (EP 1697005) or also paracetamol (EP 207 193).

2-[2-[(2,6-dichlorophenyl)-amino]-phenyl] acetic acid (diclofenac) belongs to the group of non-steroidal antirheumatic substances (NSAIDS). They inhibit non-selectively the cyclooxygenases (COX) I and II which are responsible in the organism for the generation of inflammation-mediating prostaglandins.

Diclofenac is a pharmaceutical substance that is used as a sodium or potassium salt in case of light to medium pain and inflammation, for example, in case of rheumatism, contusions, strain traumata, and arthrosis. Chemically, it belongs to the phenyl acetic adds. Diclofenac exhibits antipyretic, analgesic, antiphlogistic and anti-rheumatic effectiveness.

SUMMARY OF THE INVENTION

In contrast to flupirtine, diclofenac is available also in combination preparations. Known brand names are, for example, Arthotece (diclofenac and misoprostol), Combaren® (codein and diclofenac), Dolo-Neurobion® and Neurofenac® (diclofenac and vitamin B combination), Flectoparin® (diclofenac and heparin), Neodolpasse® (diclofenac and orphenadrine), Tobrafen (diclofenac and tobramycin), Voltamicin (diclofenac and gentamicin). A medication combination of diclofenac with a selective potassium channel opener (SNEPCO) is however not yet Known.

The simultaneous administration of flupirtine maleate and various NSAIDS is discussed in a scientific publication (Diamantis, W; Gordon, R. Postgrad Med J 1987, 63 Suppl 3 (29-34). Already at a very low dosage (15 mg per kg, mice; 35 mg per kg, rat) flupirtine maleate enhances in combination with various dosages of NSAIDS analgesics the antinociceptive (i.e., pain perception inhibiting) activity of paracetamol, acetyl salicylic acid, and diclofenac.

The synergistic combination of flupirtine salts with various non-steroidal antiphlogistic agents is disclosed in DE 3 665 538 Here it was found that the action of flupirtine maleate is surprisingly enhanced synergistically by combination with certain non-steroidal antiphlogistic substances wherein at the same time the action of the antiphlogistic agents is also experiencing a synergistic increase. In this connection, flupirtine is used as maleate, gluconate, or hydrochloride.

The purely physical mixture of individual components of flupirtine salts and diclofenac sodium, as described in DE 36 65 538.4, exhibits different solubility and different dissolving speeds of the individual components so that a uniform absorption from the gastrointestinal tract cannot be achieved. Moreover, substance separation is observed due to the different crystal forms and different densities of the active ingredients. A stable formulation of components with satisfactory bioavailability is therefore not to be expected for these mixtures.

By the formation of a multicomponent crystal of an active ingredient with a suitable second active ingredient, a new solid is formed whose physical properties differ significantly from those of the individual components. Affected parameters in this context are inter aha the solubility, dissolving speed, melting point as well as particle shape and size.

EP 2 123 626 A1 claims co-crystals of duloxetine with at least one co-crystal former that is suitable for pain treatment. Duloxetine is an active ingredient of the group of selective serotonin-norepinephrine reuptake inhibitors and is used inter aha for the treatment of depressions and anxiety disorders. A co-crystal of duloxetine and S-naproxen is mentioned as a co-crystal.

Multicomponent crystals also differ from their purely physical mixture of the two partners with regard to crystallographic and spectroscopic properties. Suitable measuring methods for the detection of solid state properties of these new compounds are inter alia X-ray powder diffraction (XRPD), solid-state nuclear magnetic resonance spectroscopy ($^{13}$C-CP/MAS-NMR) or also differential scanning calorimetry (DSC).

The object of the present invention is to provide a new substance which exhibits the unique analgesic action of the selective potassium channel opener (SNEPCO) flupirtine as well as the inflammation-inhibiting and analgesic activity of diclofenac and which can be easily formulated as a pharmaceutical solid administration form without exhibiting the typical problems of physical mixtures such as different bioavailability or separation during the production process.

Moreover, the new medication form should be acting effectively against pains caused inter alia by tension as well as those that are caused by inflammatory processes so that the treating physician can administer the medication even for pains of unclear genesis and does not expose the patient thereby to additional unacceptable side effects.

The object is solved according to the invention by a novel multicomponent crystal of ([2-amino-6-(4-fluoro-benzylamino)-pyridin-3-yl] carbamic acid ethyl ester (flupirtine) and 2-[2-[(2,6-dichlorophenyl)-amino]-phenyl] acetic acid (diclofenac), in particular by a multicomponent crystal that contains as the sole active ingredient combination the components ([2-amino-6-(4-fluoro-benzylamino)-pyridin-3-yl] carbamic acid ethyl ester (flupirtine) and 2-[2-[(2,6-dichlorophenyl)-amino]-phenyl] acetic acid (diclofenac).

Multicomponent crystal in the meaning of the invention is to be understood as a crystal that is comprised either of neutral or of ionic components wherein neutral components are used for crystallization but during crystallization to the multicomponent crystal also ionic components may be generated. A multicomponent crystal thus either is a co-crystal, a salt, a solvate or a mixed form that comprises co-crystal as well as salt proportions.

A co-crystal in the meaning of the invention is a crystalline sticture which is comprised of two or more neutral compounds.

In contrast to a purely physical mixture of the starting materials, a multicomponent crystal according to the invention is characterized advantageously by changed physico-chemical properties which, for example, affect the solubility, stability, hygroscopicity, handling, and tablet-forming property, and that enable its unequivocal characterization.

Surprisingly, the inventors have found that, by heating a solution of flupirtine with a solution of diclofenac, a novel multicomponent crystal, a co-crystal of ([2-amino-6-(4-fluoro-benzylamino)-pyridin-3-yl] carbamic acid ethyl ester (flupirtine) and 2-[2-[(2,6-dichlorophenyl)-amino]-phenyl] acetic acid (diclofenac), can be formed that subsequently will crystallize upon cooling of the solution. This is surprising because, up to now, only the unbranched alkane (or alkene) carboxylic adds from the group of carboxylic acids yielded flupirtine salts. Even with the structurally similar benzoic acid, no salts or co-crystals could be obtained together with flupirtine.

In one embodiment, the multicomponent crystal according to the invention of flupirtine and diclofenac is characterized by an X-ray powder diffractogram, measured by using Cu-$K_{\alpha 1}$ radiation and a Johansson monochromator of germanium single crystal with a step width of 0.00922° in the diffraction angle range of 2θ=3–80°, with a characteristic peak at 2θ=6.1±0.2 °.

Preferably, the multicomponent crystal is additionally characterized by further characteristic peaks at 2θ=4.9±02°, 7.7±0.2°, and 19.6±0.2°. Especially preferred, it has additionally further characteristic peaks at 2θ=11.1±0.2°, 12.3±0.2°, 14.6±0.2°, 20.9±0.2°, 22.5±0.2°, 24.2±0.2° and 24.8±0.2°.

In a preferred embodiment, the multicomponent crystal according to the invention of flupirtine and didofenac is characterized by an X-ray powder diffractogram, substantially to as shown in FIG. 1.

Moreover, the multicomponent crystal according to the invention of flupirtine and diclofenac is preferably characterized by a DSC (differential scanning calorimetry) thermogram, substantially as shown in FIG. 2. It exhibits in the range of 50 to 300° C. a characteristic melting endothermic peak in the range of 100 to 115° C. with an onset temperature of 96.9±2° C. and a peak maximum at 107.2° C.±3° C.

Preferably, the multicomponent crystal according to the invention of flupirtine and diclofenac is characterized moreover by an IR spectrum (KBr pellet) which has characteristic peaks at 3,431±1 cm$^{-1}$, 3,221±1 cm$^{-1}$, 2,989±1 cm$^{-1}$, 1,688±1 cm$^{-1}$, 1,576±1 cm$^{-1}$, 1,507±1 cm$^{-1}$, 1,453±1 cm$^{-1}$, 1,381±1 cm$^{-1}$, 1,259±1 cm$^{-1}$, 1,156±1 cm$^{-1}$, 1,126±1 cm$^{-1}$, 1,069±1 cm$^{-1}$, 832±1 cm$^{-1}$, and 776±1 cm$^{-1}$. Preferably, the multicomponent crystal of flupirtine and diclofenac according to the invention is characterized by an IR spectrum that matches substantially that of FIG. 3.

Preferably, the novel multicomponent crystal of flupirtine and diclofenac is comprised of equimolar quantities of the two components wherein also minimal deviations of up to 10%, preferably of up to 5%, particularly preferred of up to 2%, of the molar ratio are still encompassed by the present invention inasmuch as they form macroscopically a uniform compound, The molar ratio of the components is thus preferably in the range of 1:0.9 to 1:1.1, preferably of 1:0.95 to 1:1.05, more preferred 1:0.98 to 1:1.02. Especially preferred, the molar ratio of the components is 1:1.

Subject matter of the invention is also a method for producing the multicomponent crystal of flupirtine and diclofenac according to the invention. Preferably, for this purpose, flupirtine in base form is added together with diclofenac to a suitable inert organic, preferably aprotic, solvent, especially preferred, toluene, and dissolved with heating, preferably to a temperature of 50 to 80° C. Subsequently, after cooling the solution to room temperature, the multicomponent crystal of flupirtine and diclofenac according to the invention is allowed to crystallize as a white, finely crystalline precipitate.

Subject matter of the invention is also a pharmaceutical preparation that contains the multicomponent crystal according to the invention.

The pharmaceutical preparation according to the invention contains novel multicomponent crystals of ([2-amino-6-(4-fluoro-benzylamino)-pyridin-3-yl] carbamic acid ethyl ester and 2-[2-[(2,6-dichlorophenyl)-amino]-phenyl] acetic acid, optionally in a mixture with other pharmacologically or pharmaceutically active substances. The manufacture of the medicaments is done in the known manner, wherein the known and conventional pharmaceutical excipients as well as other conventional carrier and diluting agents may be used.

Methods for determining an effective administration quantity of the preparation according to the invention for therapeutic and prophylactic purposes are known to a person of skill in the art. In order to be able to employ the analgesic action (inter alia by affecting the muscle tension pain) as well as the anti-inflammatory action of the preparation according to the invention, a daily dosage of 50 mg to 1,000 mg, preferably 200 mg to 800 mg, is administered.

The new multicomponent crystal according to the invention of ([2-amino-6-(4-fluoro-benzylamino)-pyridin-3-yl] carbamic acid ethyl ester and 2-[2-[(2,6-dichlorophenyl)-amino]-phenyl] acetic add has, as a result of its physical properties, surprising properties in respect to its galenic processing to solid medicament forms. By means of the new multicomponent crystal according to the invention, the pharmaceutically inactive components of the base compound (such as maleate, hydrochloride, mesilate etc.) as well as of the acid component (such as sodium or potassium) that are usually present in purely physical mixtures are avoided which advantageously, in case of solid oral administration forms, leads to a reduction of the quantity to be administered and the required volume of the administration form. The uniform shape of the multicomponent crystal prevents advantageously also the separation of the components during processing and facilitated in this way their exact dosage.

An administration unit can be administered, for example, 1 to 5 times, preferably 1 to 3 times, preferably 2 times daily.

The pharmaceutical preparation according to the invention can be administered in various ways known from pharmacology or medicine, for example, orally, parenterally, intraperitoneally, intravenously, sublingually, intramuscularly, rectally, transdermally, subcutaneously, intraadiposally, intraarticularly or intrathecally. Preferred is oral administration of the pharmaceutical preparation.

Suitable administration forms for oral administration include tablets, effervescent tablets, capsules, soft capsules, pills. powders, granulates, pellets and the like.

The release of the active ingredients from the pharmaceutical preparation according to the invention can happen quickly or with retardation.

As a pharmaceutically acceptable carrier or filler various conventional excipients such as cellulose derivatives, starch derivatives, lactose, mannitol, dextrose, saccharose, calcium carbonate, magnesium oxide, magnesium stearate, talcum, starch, gelatine, gum Arabic, or the like or conventional inert solvents can be used.

Solid administration forms comprise optionally further conventional excipients such as glidants, binding agents, filling agents (for example, silicon dioxide, in particular porous amorphous silicon dioxide "Syloid", carbomer, guar gum, cellulose, microcrystalline cellulose, the cellulose ethers, cellulose esters, polyvinyl pyrrolidone as well as copovidone), release agents, lubricants, disintegrants (such as cross-linked polyvinyl pyrrolidone, sodium carboxyl methyl starch, sodium carboxyl methyl cellulose, starch, croscarmellose sodium, crospovidone, guar gum, prirnogel), antioxidants, flavoring agents, dyes, solutizers (for example, cyclodextrine and cyclodextrine derivatives) and/or emulsifiers (such as e.g. lecithin, pectin).

The solid administration forms can be coated with sucrose, with a cellulose derivative, polyacrylate derivative, phthalate derivative or other suitable substances or they can be treated such that they have an extended or retarded action so that they continuously release a predetermined quantity of an active ingredient.

The invention comprises therefore also a pharmaceutical preparation that is characterized by a polymer film coating that acts as a retarding component and optionally contains release agents, binding agents, pigments or other pharmaceutical excipients. Preferably, the polymer film coating comprises at least one polymer selected from methacrylic acid, methacrylic ester (such as Eudragit®L and/or Eudragit®S), copolymers of acrylic and methacrylic acid esters, copolymers of acrylic acid and methacrylic acid as well as their esters, or mixtures thereof.

By dissolving or suspending, liquid formulations can be obtained also that are suitable for infusion or injection.

As a non-aqueous solvent, for example, propylene glycol, polyethylene glycol and/or organic esters such as ethyl oleate can be used. Examples of oils are paraffin oil as well as animal, plant or synthetic oils, for example, peanut oil, castor oil, sesame oil, cotton seed oil, corn oil, wheat germ oil, soybean oil, mineral oil, olive oil, sunflower seed oil or liver oil, in particular cod liver oil.

By mixing with non-aqueous solvents or oils, viscous to semi-solid formulations can be obtained which can be filled in particular into soft capsules. These capsules, despite their relatively high active ingredient contents of 100 to 800 mg, can be easily swallowed as a result of their elastic envelope and consistency of the content.

For the new multicomponent crystal of the active ingredients flupirtine and diclofenac according to the invention, a mixture of glycol derivatives, for example, diethylene glycol monoethylether or polyethylene glycol, surfactants such as e.g. glycerin derivatives, as well as thickening agents, for example, polyvinyl pyrrolidone has been found to be a suitable carrier substance for a soft capsule formulation. Neutral solutizers (dispersants and surfactants) such as glycerides (also polyoxylglycerides), poly alkylene glycol ether caprylocaproyl, or sugar esters stabilize and homogenize the mixtures with the active ingredients according to the invention.

Due to the minimal polarity of the new multicomponent crystal of the active ingredients flupirtine and diclofenac according to the invention, liquid and semi-solid formulations are suitable also for the transdermal administration, quite in contrast to a mixture of the components flupirtine maleate and diclofenac sodium. Particularly suitable as a carrier for the multicomponent crystal of the active ingredients flupirtine and diclofenac according to the invention is a mixture comprising a carbomer, one or several fatty acid esters, a polyethylene glycol and one or several low-molecular weight alcohols.

Surprisingly, in accordance with the method disclosed in DE 19 705 555 A1, by mixing the active ingredient with porous amorphous silicon dioxide a granulate can be obtained that can be pressed without problems to tablets with up to 600 mg active ingredient. In one embodiment of the invention, the multicomponent crystal of the active ingredient flupirtine and diclofenac according to the invention is contained in a tablet that preferably contains also a pharmaceutically acceptable filler, for example, such as e.g. amorphous silicon dioxide. Preferably, in one tablet 0.5-8% by weight of porous amorphous silicon dioxide are contained, based on the total weight of the tablet The synergistic action of the two components flupirtine and diclofenac can be demonstrated by animal model with the methods disclosed in DE 36 65 538. The methods disclosed therein are herewith incorporated as a reference, The effects that are obtained with the co-crystals (salts) according to the invention in pain and inflammation model are qualitatively comparable to the test results of DE 36 65 538. In combination with the advantages of the formulation, the multicomponent crystal of the active ingredients flupirtine and diclofenac according to the invention is significantly superior in comparison to the purely physical mixture of the individual components.

An aspect of the invention is also the use of the multicomponent crystal according to the invention for treatment and prophylaxis of acute and chronic pains, including neuropathic pain, back pain, nerve pain, pain caused by cancer diseases, vasomotoric and/or migraine pain or tension-caused headaches, pain conditions after operations, after injuries, burns. chemical burns, in case of dysmenorrhea, prophylaxis of muscle tension, toothache and arthritic pain inasmuch as an inflammatory component of the pain is not excluded. The preferred administration duration is 1-2 days up to 6 weeks.

With the advantageous combined action against the inflammation-caused pain (such as e.g. muscle tension-caused pain) and inflammatory pain, the new active ingredient is particularly well suited for treatment of pain of the musculoskeletal system of unclear genesis, including the back, because, as is well known, here particularly inflammatory processes and muscle tension occur frequently.

For example, tablets of different sizes can be produced, for example, with a total weight of approximately 50 to 800 mg. They contain the complex active ingredient in the aforementioned quantities and usual carriers and/or dilution agents and/or excipients. These tablets can be provided also for administration of partial dosages. In analogous manner, for example, also other preparations, for example, gelatin capsules or retard forms, can be formulated.

For a fast dissolving action and improved bioavailability, the new multicomponent crystal of the active ingredients flupirtine and diclofenac according to the invention can also be administered in soft capsules. The active ingredients are homogenously distributed in a soft gel matrix, i.e., suspended, dissolved or partially dissolved. Despite additional ingredients, these capsules can be easily swallowed as a result of the soft shell.

BRIEF DESCRIPTION OF THE DRAWINGS

Based on the following Figures and embodiments the invention will be explained in more detail without limiting it It is shown in.

DESCRIPTION OF PREFERRED EMBODIMENTS

EXAMPLE 1

Preparation of a multicomponent crystal according to the invention of ([2-amino-6-(4-fluoro-benzylamino)-pyridin-3-yl] carbamic acid ethyl ester and 2-[2-[(2,6-dichlorophenyl)-amino]-phenyl]acetic acid 12.0 g of ([2-amino-6-(4-fluoro-benzylamino)-pyridin-3-yl] carbamic acid ethyl ester (flupirtine) and 11.8 g of 2-[2-[(2,6-dichlorophenyl)-amino]-phenyl] acetic add (diclofenac) are added under argon atmosphere to 500 ml toluene and the mixture is heated to 60° C. and maintained at 60° C. for further minutes, After cooling to 20° C. the solution is allowed to rest overnight. During this time, a white finely crystalline precipitate forms. The latter was filtered off and dried in vacuum for 12 hours. As a product, 15.7 g (66%) white crystal needles were obtained. The product melts at a temperature of 101 to 103° C.

Figure 4:
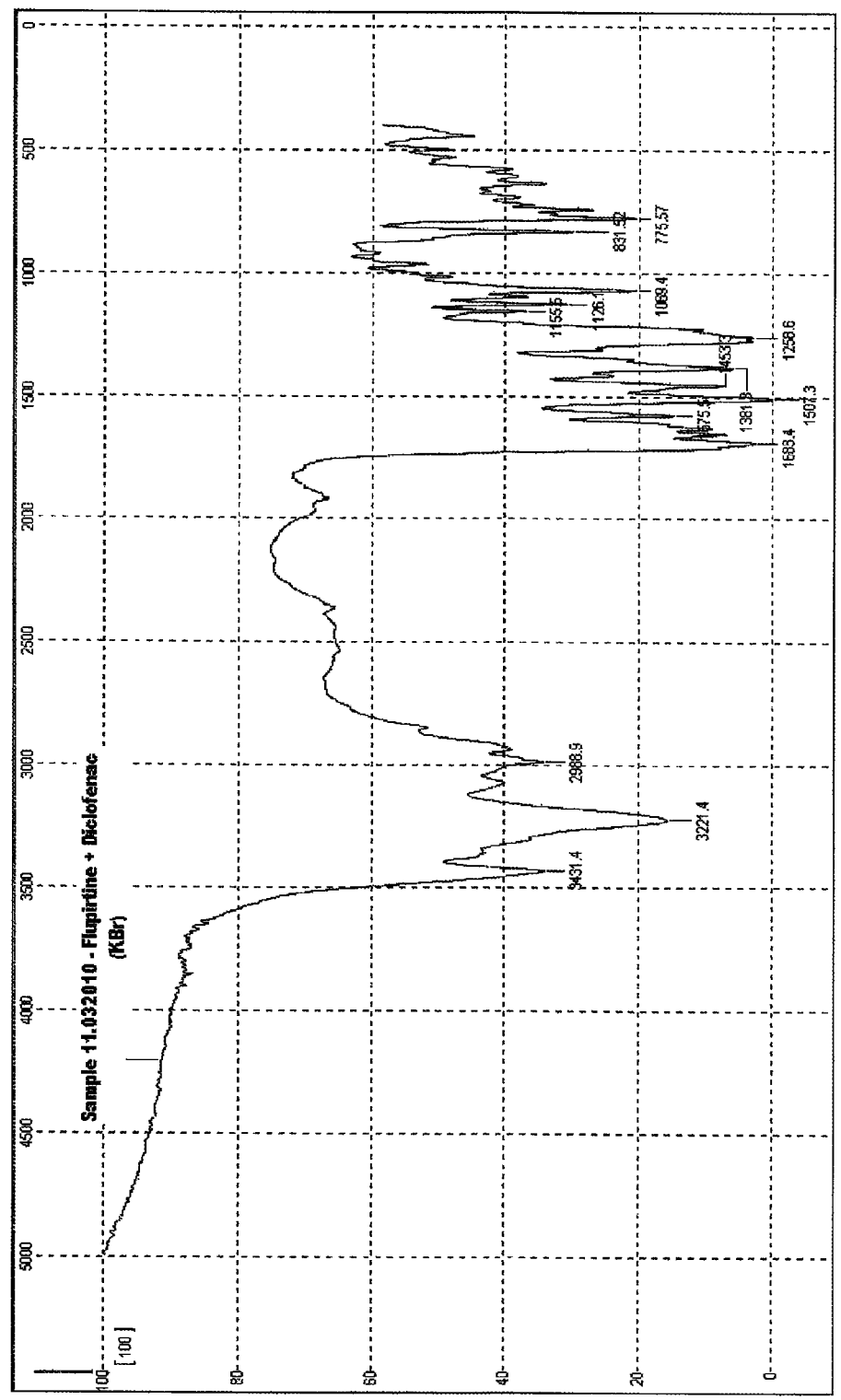
FIG. 4 an IR spectrum of the multicomponent crystal of the active ingredients flupirtine and diclofenac according to the invention.
Figure 5:
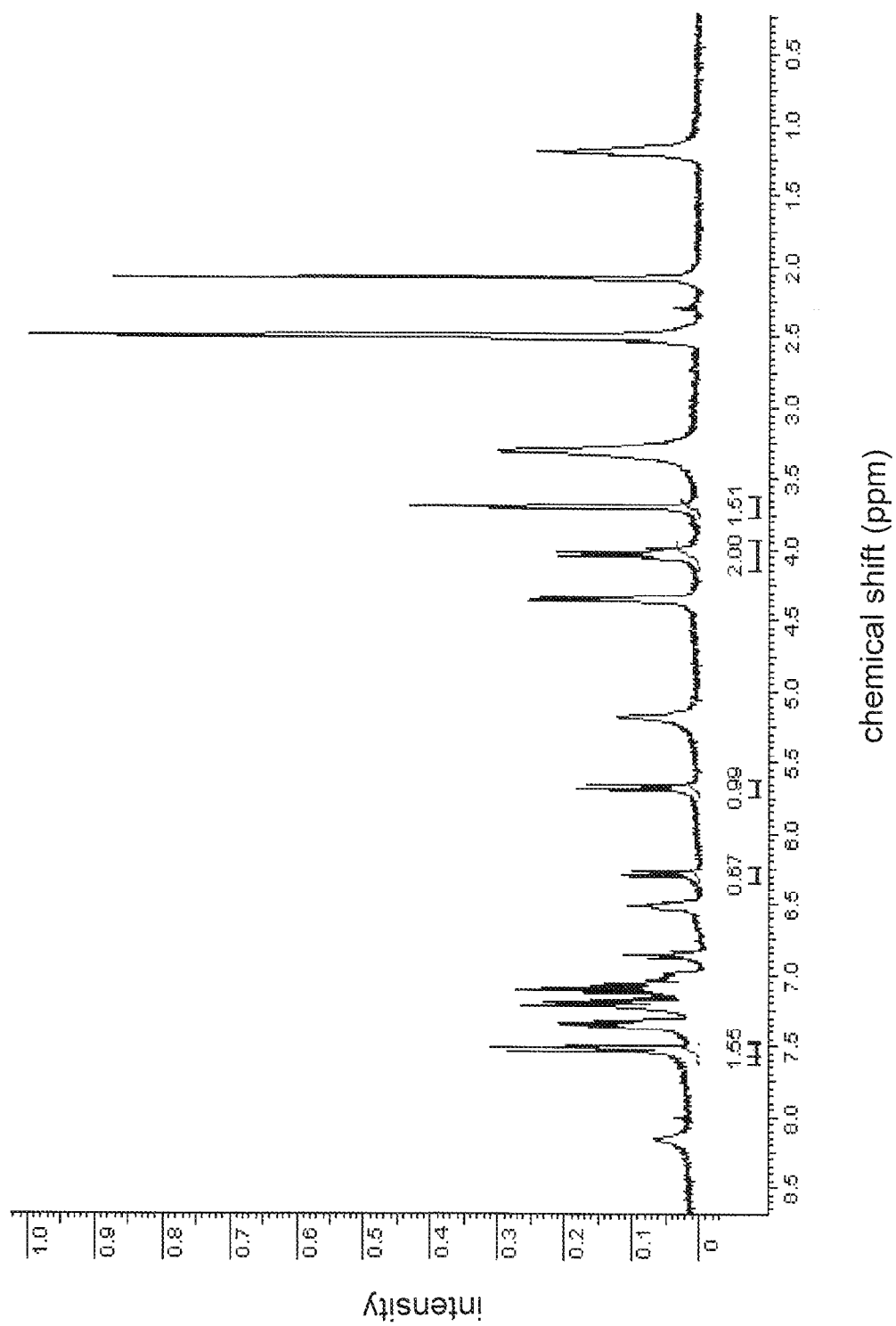
FIG. 5 an 1H NMR spectrum of the multicomponent crystal of the active ingredients flupirtine and diclofenac according to the invention.

The structure of the multicomponent crystal was confirmed by IR spectrum (FIG. 4) and 1H NMR spectrum (DMSO-d6; 400 MHz) (FIG. 5).

EXAMPLE 2

Analysis of the Multicomponent Crystal by Means of X-Ray Powder Diffraction

The X-ray powder diffraction analysis of the compound obtained according to Example 1 was carried out by means of a D8 Advance powder diffractometer of the company Bruker AXS: its specifications and the measuring parameters are compiled in Table 1.

TABLE 1

Device specifications and measuring parameters for the X-ray powder diffraction.

| Device specifications | |
|---|---|
| Monochromator | Johansson germanium single crystal |
| Detector | PSD LynxEye data recording report 4° 2θ |
| Sample carrier | Capillary sample carrier with a capillary diameter of 0.5 mm |
| Measuring parameters | |
| Radiation | Cu $K_{\alpha 1}$ |
| Generator | 40 kV, 40 mA |
| Angle range | 3° to 80° 2θ |
| Step width | 0.00922° 2θ |
| Measuring duration | 3 seconds per step |

Figure 1:
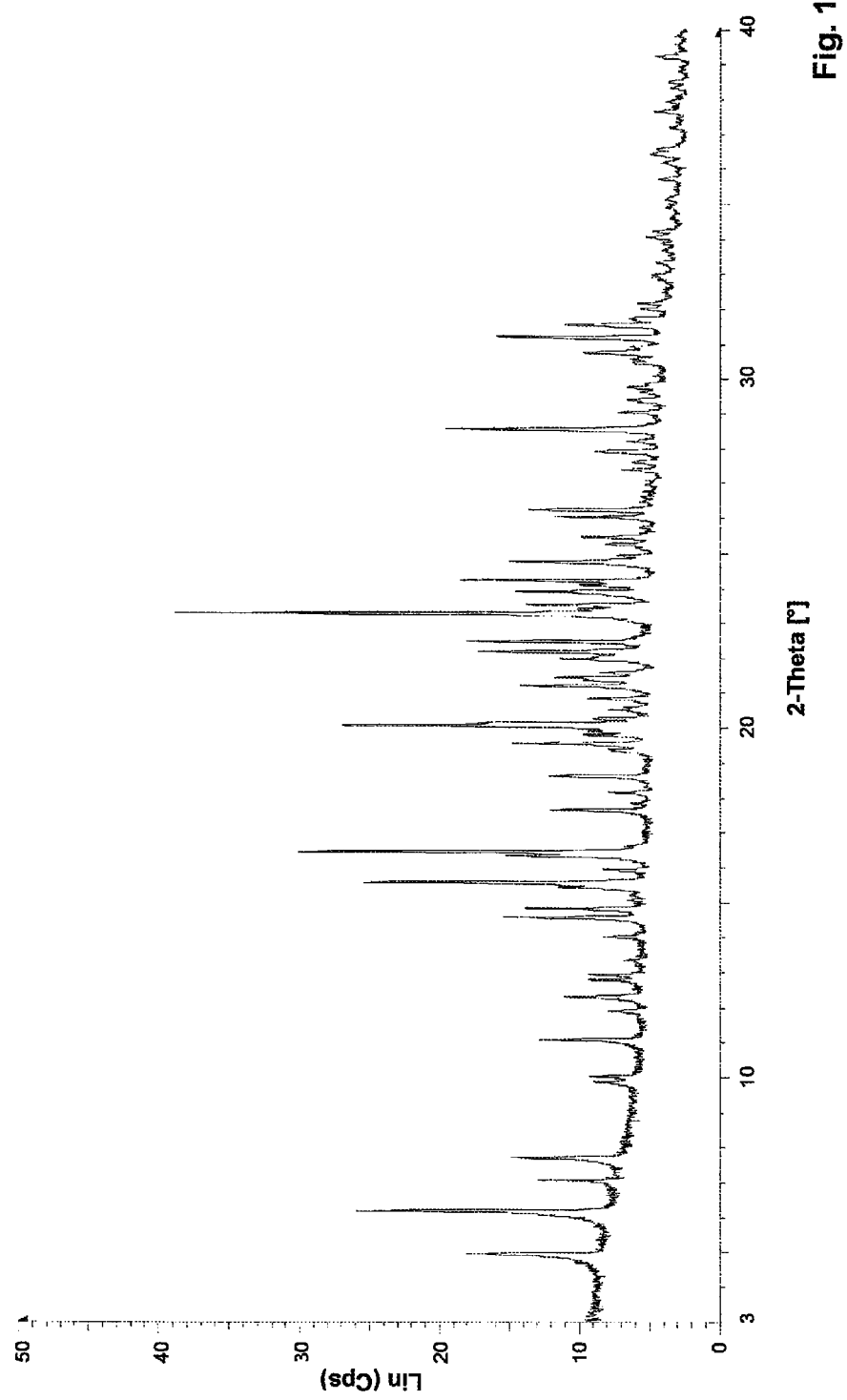
FIG. 1 an X-ray powder diffractogram of the multicomponent crystal of flupirtine and diclofenac.
Figure 2:
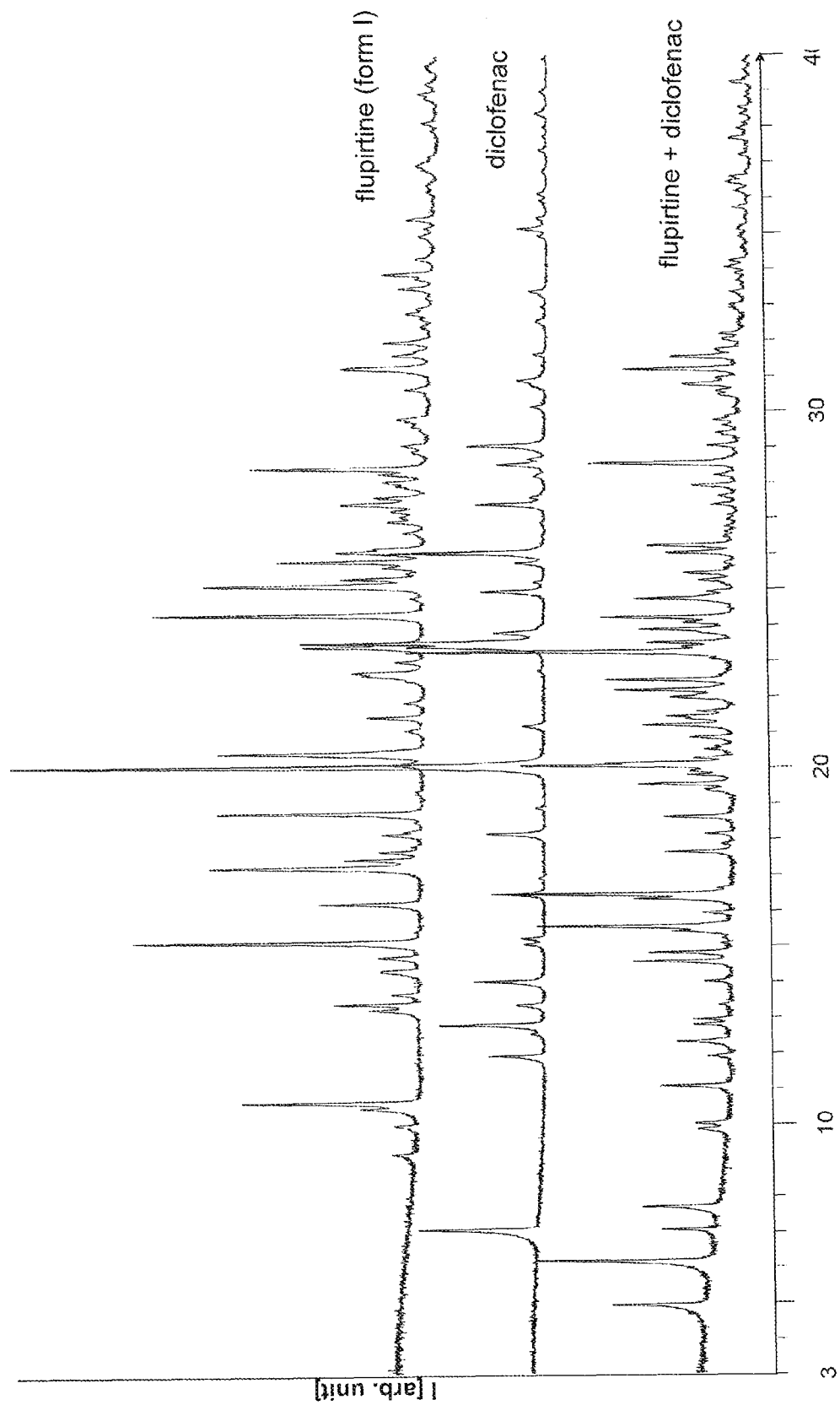
FIG. 2 the X-ray powder diffractograms of diclofenac, of flupirtine, and of the multicomponent crystal of flupirtine and diclofenac, in comparison.

The X-ray powder diffractogram determined in this manner is illustrated in FIG. 1. A comparison between the diffractograms of the multicomponent crystal and the components ([2-amino-6-(4-fluoro-benzylamino)-pyridin-3-yl] carbamic acid ethyl ester and 2-[2-[(2,6-dichlorophenyl)-amino]-phenyl] acetic acid used for its preparation is illustrated in FIG. 2

The signal positions of the X-ray powder diffractogram for the multicomponent crystal of flupirtine and diclofenac obtained according to Example 1 are compiled in Table 2.

TABLE 2

Signal positions of the X-ray powder diffraction spectrum for flupirtine-diclofenac according to Example 1

| 2Theta/° | Relative intensity/% |
|---|---|
| 4.90 | 47 |
| 6.14 | 67 |
| 7.67 | 38 |
| 11.06 | 33 |
| 12.29 | 28 |
| 14.56 | 40 |
| 19.55 | 38 |
| 20.85 | 24 |
| 22.48 | 46 |
| 24.23 | 48 |
| 24.75 | 39 |

EXAMPLE 3

Analysis of the multicomponent crystal by means of DSC (differential scanning calorimetry)

The thermogram of the compound obtained according to Example 1 was measured by a NETSCH DSC 204 F1 Phönix. The specifications are listed in Table 3.

TABLE 3

Device specifications and measuring parameters
for DSC (differential scanning calorimetry)

| Device specifications | |
|---|---|
| Measuring sensor | τ sensor |
| Furnace | Silver block with miniature jacket heating element |
| Cooling system | Mechanical cooling (intracooler) |
| Sample carrier | Aluminum sample crucible, crucible diameter 6 mm |
| Measuring parameters | |
| Heating rate | 10° C. per min. |
| Temperature program | 20° C.-300° C. |
| Inert gas | nitrogen |
| Gas flow rate | 20 ml/min. |
| Sample mass | 7.872 mg |

Figure 3:
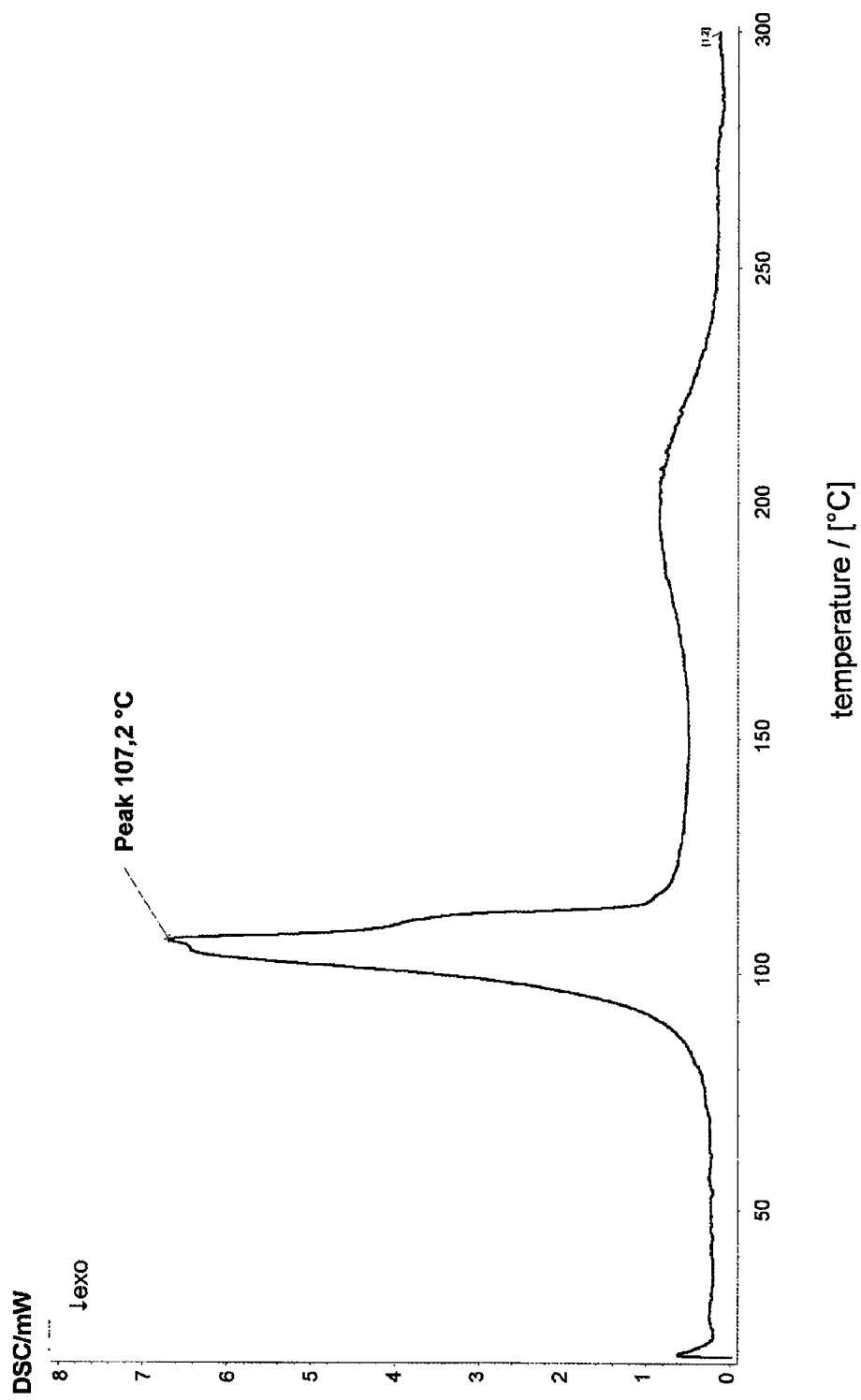
FIG. 3 a DSC (differential scanning calorimetry) thermogram of the multicomponent crystal of flupirtine and diclofenac.

The evaluation of the thermograms was carried out with the program Proteus (version 4.8.5) of the company NETZSCH. The obtained thermogram is shown in FIG. 3.

EXAMPLE 4

Analysis of the Multicomponent Crystal by Means of $^{13}$C CP/MAS NMR

All spectra were measured on an Avance 400 (company BRUKER, Rheinstetten) at a $^{13}$C resonance frequency of 100.62 MHz. During measuring, the samples were rotated in a 4 mm double resonance sample head at a rotation frequency of 10.0 kHz ("magic angle spinning", MAS), For the CP experiment ("cross polarization", CP), a $^1$H 90° pulse of 5.23 μs and a contact pulse of 10 ms duration were used. The spectral width was 250 ppm (25,252 Hz).

13,000 FIDs with a repetition rate of 5.0 s were accumulated. In this connection, 1,600 data points were recorded and Fourier-transformed with a total point number of 16,384 ("zero-filling").

The chemical shift relates to tetramethyl silane (TMS, $s_{TMS}$=0.0 ppm). As a reference, after each experiment adamantine as a secondary external standard was measured ($s_{adamantane}$=28.72, 37.77 ppm).

Figure 6:
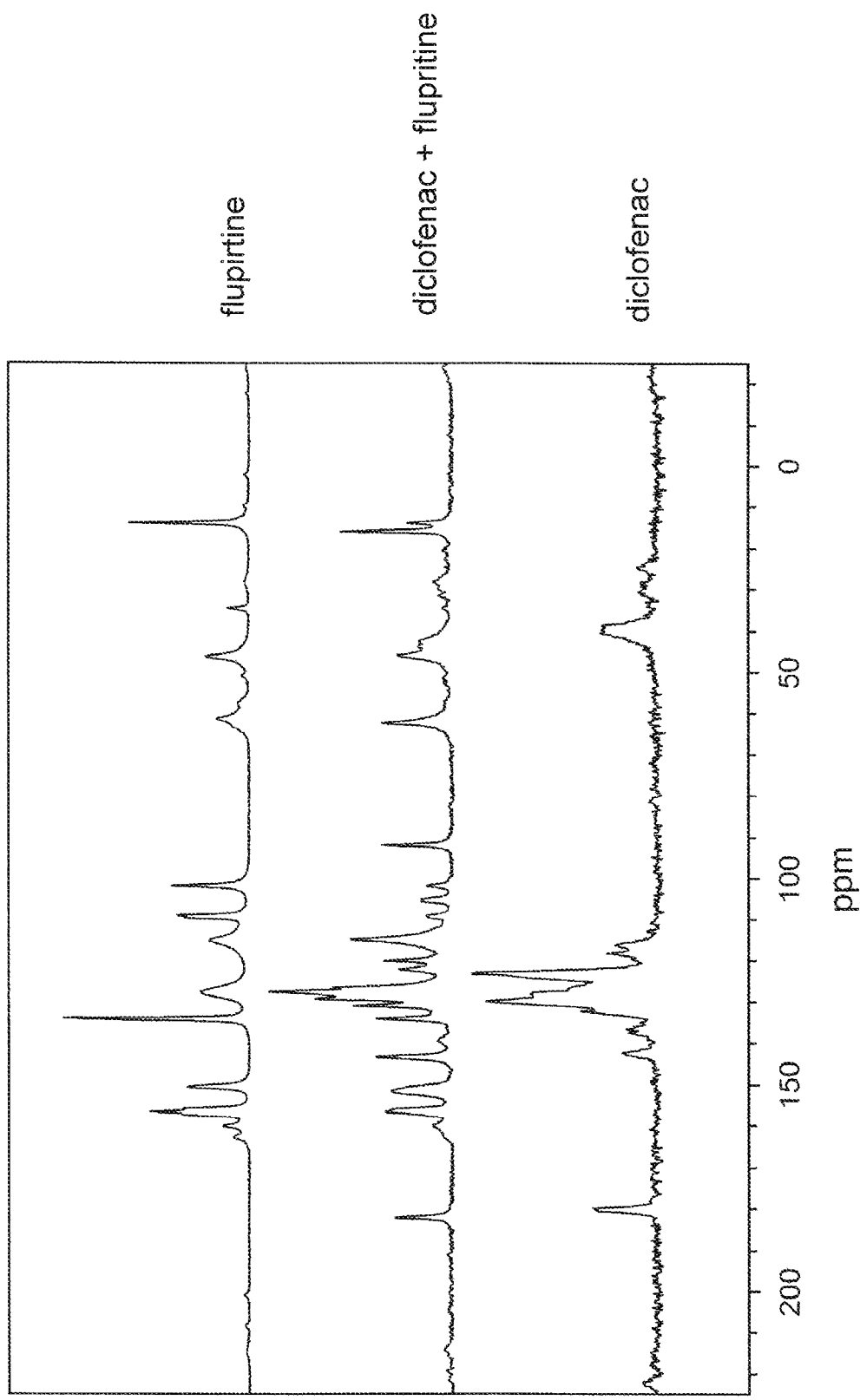
FIG. 6 a $^{13}C$ CPMAS NMR spectrum of the multicomponent crystal of the active ingredients flupirtine and diclofenac according to the invention.

The $^{13}$C CP/MAS NMR spectra of the multicomponent crystal as well as of the starting components ([2-amino-6-(4-fluoro-benzylamino)-pyridin-3-yl] carbamic acid ethyl ester and 2-[2-[(2,6-dichlorophenyl)-amino]-phenyl] acetic acid are shown in FIG. 6.

EXAMPLE 5

Soft Capsules Containing 150 mg of the Multicomponent Crystal of ([2-amino-6-(4-fluoro-benzylamino)-pyridin-3-yl] Carbamic Acid Ethyl Ester and 2-[2-[(2,6-dichlorophenyl)-amino]-phenyl] Acetic Acid According to the Invention 150 mg of the multicomponent crystal according to the invention of flupirtine and diclofenac produced according to Example 1 are mixed, optionally with light heating, with 300 mg of diethylene glycol monoethylether, 100 mg of polyethylene glycol, and 15 mg of polyvinyl pyrrolidone and 90 mg Labrasol® and filled into soft gelatin capsules.

What is claimed is:

1. Multicomponent crystal, characterized in that it consists of ([2-amino-6-(4-fluoro-benzylamino)-pyridin-3-yl] carbamic acid ethyl ester (flupirtine) and 2-[2-[(2,6-dichlorophenyl)-amino]-phenyl] acetic acid (diclofenac), wherein the molar ratio of ([2-amino-6-(4-fluoro-benzylamino)-pyridin-3-yl] carbamic acid ethyl ester and 2-[2-[(2,6-dichlorophenyl)-amino]-phenyl] acetic acid is in the range of 0.9 : 1 to 1.1 : 1.0, further characterized by an X-ray powder diffractogram with a characteristic peak at 2θ=6.1±0.2° and additionally characterized by an X-ray powder diffractogram with a characteristic peak at 2θ=4.9±0.2°, 7.7 ±0.2°, and 19.6±0.2°.

2. Multicomponent crystal according to claim 1, additionally characterized by an X-ray powder diffractogram with a characteristic peak at 2θ=11.1±0.2°, 12.3±0.2°, 14.6±0.2°, 20.9±0.2°, 22.5±0.2°, 24.2±0.2° and 24.8±0.2°.

3. Multicomponent crystal according to claim 1, characterized by a DSC thermogram with a melting endothermal peak in the range of 100 to 115° C. with an onset temperature of 96.9±2° C. and with a peak maximum at 107.2° C.±3° C.

4. Method for producing a multicomponent crystal according to claim 1, comprising the steps:
   a) dissolving of ([2-amino-6-(4-fluoro-benzylamino)-pyridin-3-yl] carbamic acid ethyl ester and 2-[2-[(2,6-dichlorophenyl)-amino]-phenyl] acetic acid in a molar ratio of 1.0 : 0.9 to 1.0 : 1.1 in an inert organic solvent and
   b) crystallizing the complex compound.

5. Pharmaceutical preparation comprising a multicomponent crystal according to claim 1 as an active ingredient combination.

6. Pharmaceutical preparation according to claim 5 in the form of a soft capsule.

7. Transdermal pharmaceutical preparation comprising a multicomponent crystal according to claim 1 as an active ingredient.

8. Oral pharmaceutical preparation according to claim 5, wherein the pharmaceutical preparation contains 50 to 1,000 mg per administration unit of said multicomponent crystal.

9. A method of treating a patient suffering from acute and chronic pains, selected from the group consisting of neuropathic pain, nerve pain, pain caused by cancer diseases, tension headaches, vasomotoric and migraine headaches, pain conditions after operations, after injuries, burns, chemical burns, dysmenorrhea pain, toothache, arthritic pain, and inflammation pain, the method comprising administering to said patient an effective amount of the multicomponent crystal of claim 1.

10. The method according to claim 9 for treating muscle tension, muscle spasm, muscle stiffness, and back pain.

11. The method according to claim 9, comprising simultaneously treating pain of different causes.

12. Method for producing a pharmaceutical preparation comprising mixing of a complex compound according to claim 1 with a glycol-containing solvent, a solutizer, and a viscosity-imparting agent, and introducing the mixture into a soft gelatine capsule.

13. Transdermal pharmaceutical preparation according to claim 7, wherein the pharmaceutical preparation contains 50 to 1,000 mg per administration unit of said multicomponent crystal.

14. A method of treating a patient suffering from acute and chronic pains, selected from the group consisting of neuropathic pain, nerve pain, pain caused by cancer diseases, tension headaches, vasomotoric and migraine headaches, pain conditions after operations, after injuries, burns, chemical burns, dysmenorrhea pain, toothache, arthritic pain, and inflammation pain, the method comprising administering to said patient an oral pharmaceutical preparation, comprising a multicomponent crystal according to claim 1 as an active ingredient combination, in an effective amount.

15. A method of treating a patient suffering from acute and chronic pains, selected from the group consisting of neuropathic pain, nerve pain, pain caused by cancer diseases, tension headaches, vasomotoric and migraine headaches, pain conditions after operations, after injuries, burns, chemical burns, dysmenorrhea pain, toothache, arthritic pain, and inflammation pain, the method comprising administering to said patient a transdermal pharmaceutical preparation, comprising a multicomponent crystal according to claim 1 as an active ingredient combination, in an effective amount.

16. A method of treating a patient suffering from muscle tension, muscle spasm, muscle stiffness, and back pain, the method comprising administering to said patient an oral pharmaceutical preparation, comprising a multicomponent crystal according to claim 1 as an active ingredient combination, in an effective amount.

17. A method of treating a patient suffering from muscle tension, muscle spasm, muscle stiffness, and back pain, the method comprising administering to said patient a transdermal pharmaceutical preparation, comprising a multicomponent crystal according to claim 1 as an active ingredient combination, in an effective amount.

18. A method of treating a patient suffering from pain of different causes, the method comprising administering to said patient a pharmaceutical preparation, comprising a multicomponent crystal according to claim 1 as an active ingredient combination, in an effective amount, wherein the pharmaceutical preparation is selected from the group consisting of an oral preparation and a transdermal preparation.

19. The method according to claim 18, wherein the pain of different causes comprises inflammatory pain and pain caused by muscle tension.

20. The method according to claim 11, wherein the pain of different causes comprises inflammatory pain and pain caused by muscle tension.

\* \* \* \* \*